(12) United States Patent
Kim et al.

(10) Patent No.: US 7,812,177 B2
(45) Date of Patent: Oct. 12, 2010

(54) POTASSIUM CHANNEL OPENER HAVING BENZOFUROINDOLE SKELETON

(75) Inventors: Yong-Chul Kim, Gwangju (KR); Chul-Seung Park, Seoul (KR); Tal-Soo Ha, Seoul (KR)

(73) Assignee: Anygen Co., Ltd., Gwangju (KR)

( * ) Notice: Subject to any disclaimer, the term of this patent is extended or adjusted under 35 U.S.C. 154(b) by 516 days.

(21) Appl. No.: 11/885,867

(22) PCT Filed: Mar. 10, 2006

(86) PCT No.: PCT/KR2006/000855

§ 371 (c)(1), (2), (4) Date: Sep. 7, 2007

(87) PCT Pub. No.: WO2006/096030

PCT Pub. Date: Sep. 14, 2006

(65) Prior Publication Data

US 2008/0194837 A1    Aug. 14, 2008

(30) Foreign Application Priority Data

Mar. 10, 2005    (KR) .................... 10-2005-0020008

(51) Int. Cl.
C07D 487/04    (2006.01)
(52) U.S. Cl. .................................... 548/421
(58) Field of Classification Search .............. None
See application file for complete search history.

(56) References Cited

U.S. PATENT DOCUMENTS 6,391,902 B2 *    5/2002    Antane et al. ............ 514/382

\* cited by examiner

*Primary Examiner*—Kamal A Saeed
(74) *Attorney, Agent, or Firm*—Kenyon & Kenyon LLP

(57) ABSTRACT

The object of the present invention is to provide a potassium channel opener having benzofuroindole skeleton representing the following formula (I) wherein, $R_1$ is hydrogen, $R_2$ is $CF_3$, $R_3$ is COOH, $R_4$ is hydrogen, $R_5$ is hydrogen or chloride and $R_6$ is hydrogen or chloride.

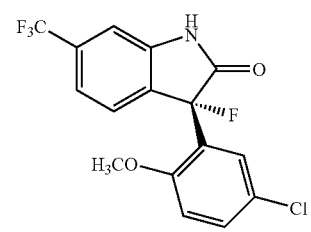

BMS-204352

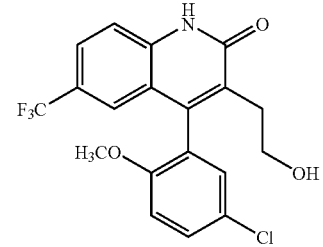

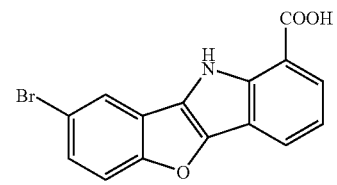

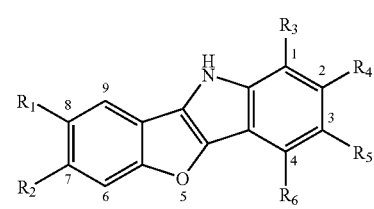

5 Claims, 6 Drawing Sheets

US 7,812,177 B2

POTASSIUM CHANNEL OPENER HAVING BENZOFUROINDOLE SKELETON

This is a 371 national phase application of PCT/KR2006/000855 filed 10 Mar. 2006, claiming priority to Korean Patent Application No. 10-2005-20008 filed 10 Mar. 2005, the contents of which are incorporated herein by reference.

TECHNICAL FIELD

The present invention relates to a potassium channel opener having benzofuroindole skeleton. More particularly, this invention relates to a novel potassium channel opener having benzofuroindole skeleton which can be produced by substituting the substituent radicals and its preparation method.

BACKGROUND ART

Potassium channels belong to a ubiquitous and heterogeneous protein family, selectively permitting $K^+$ ions to move across the cell membrane. These channels play an important role in adjusting cellular excitability through maintenance of the optimum set of conditions for $K^+$ ion and its various effects on membrane potential and membrane resistance. There are different kinds of $K^+$ channel in human body, which are activated by different mechanism. By considering the different factors influencing on the activity of different classes of $K^+$ channels, calcium-activated potassium channels are the one, of which opening was determined by the raise of the intracellular calcium concentrations, and regulated by transmenbrane voltage and phosphorylation states.

Calcium-activated potassium channels are further divided into three major types, which can be distinguished electropysiologically by their different single-channel conductance.

The $BK_{Ca}$ (or Maxi-K) channel has the particular function of large single-channel conductance (100~250 pS), whereas other two major types of calcium dependent potassium channels are small conductance 92~25 pS, $SK_{Ca}$) and intermediate conductance group (25~100 pS, $IK_{Ca}$). Among these three kinds of channels, $BK_{Ca}$ channel is particularly regarded because of the extensive $K^+$ efflux and membrane hyperpolarization due to their large single-channel conductance, and their expression in a range of non-excitable and excitable cell types including neurons and muscles. Especially, $BK_{Ca}$ channels play roles in shaping action potentials and regulating neuronal excitability and neuro-transmitter release in nervous system.

The therapeutic potentials of $BK_{Ca}$ channel are more evident in pathological conditions such as potential neurotoxic cascade introduced by excess $Ca^{2+}$ entry, which could be limited or interrupted by $BK_{Ca}$ channel activators or openers. Thus, designing chemical openers of $BK_{Ca}$ channel would be a strategy for the development of drugs to treat neuronal damages resulted from traumatic and ischemic events or neuro-degenerative processes.

Also, the vaso-relaxation effects of $BK_{Ca}$ channel openers could be utilized to develop drugs to treat cardiovascular diseases or hypertension, airway smooth muscle related disease such as asthma and erectile dysfunctions.

$BK_{Ca}$ channels are composed of two different subunits: the pore forming α subunit and the auxiliary β subunits. Although channels formed only by four α subunits can be functional, β subunits alter the biophysical and pharmacological properties of homomeric channels, including $Ca^{2+}$ and voltage sensitivity, and gating kinetics.

Several compounds have been developed and reported to be $BK_{Ca}$ channel openers (e.g., dehydrosoyasaponin-I, maxikdiol, NS-1619, BMS-204352, 17-β-estradiol, ethylbromide tamoxifen, pimaric acid and epoxyeicosatrienoic acid). Although some synthetic activators, such as, NS-1619 and BMS-204352, act on the α subunit, other openers of $BK_{Ca}$ channels, including dehydrosoyasaponin-I and 17-β-estradiol, require β subunit for their action. Several activators derived from natural products such as dehydrosoyasaponin-I are impermeable to the cell membrane and act only on intracellular side of $BK_{Ca}$ channels.

In U.S. Pat. No. 6,288,099, the skeleton of benzofuroindole and its derivatives have been disclosed as calcium channel opener. However, in this disclosure, only whole skeleton of benzofuroindole and its broad derivatives have been suggested without specifying the selective substituent.

Among the prototypical $BK_{Ca}$ channel openers 1 (BMS-204352), quinolinone analog 2 and substituted benzofuroindole analog 3, compound 1 was reported to selectively shift the $BK_{Ca}$ channel activation curve toward less positive membrane potentials in a dose dependent manner and currently in clinical trials targeting acute ischemic stroke.

Benzofuroindole analog 3 was studied as a $BK_{Ca}$ channel opener to show bladder selective smooth muscle relaxation effect and increasing outward current in voltage clamp experiment on isolated rat bladder smooth muscle cells. However, no further results have been reported regarding the structural activity or biological property in the duplicated $BK_{Ca}$ channel.

DISCLOSURE OF INVENTION

The object of the present invention is to provide a potassium channel opener having benzofuroindole skeleton representing the following formula (I).

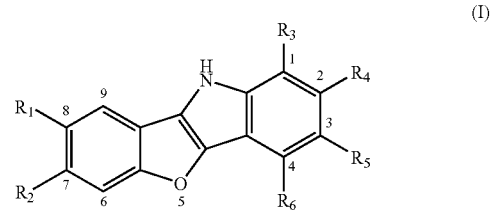

wherein, $R_1$ is hydrogen, $R_2$ is $CF_3$, $R_3$ is COOH, $R_4$ is hydrogen, $R_5$ is hydrogen or chloride and $R_6$ is hydrogen or chloride.

Further, the present invention provide a compound wherein it comprises that $R_1$ is hydrogen, $R_2$ is $CF_3$, $R_3$ is COOH, $R_4$ is hydrogen, $R_5$ is hydrogen and $R_6$ is hydrogen; a compound wherein it comprises that $R_1$ is hydrogen, $R_2$ is $CF_3$, $R_3$ is COOH, $R_4$ is hydrogen, $R_5$ is hydrogen and $R_6$ is chloride; a compound wherein it comprises that $R_1$ is hydrogen, $R_2$ is $CF_3$, $R_3$ is COOH, $R_4$ is hydrogen, $R_5$ is chloride and $R_6$ is hydrogen.

Further, the present invention provide a process for preparing a potassium channel opener having benzofuroindole skeleton representing the following formula (I), which comprises the steps of:

i) preparing compound of formula (III) by reacting and condensing salicylic acid derivatives represented by formula (II) as starting material

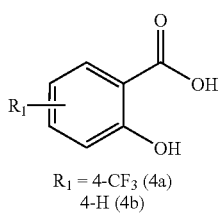

$R_1$ = 4-CF$_3$ (4a)
4-H (4b)

with ethylbromoacetate in the present of sulfuric acid added methanol solvent leaving the hydrogen bromide subsequently and leaving the ethyl group by NaOH aqueous solution;

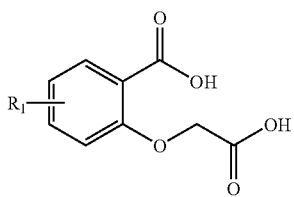

ii) preparing compound of formula (IV) by cyclization reaction through the reflux of compound of formula (III) in the presence of acetic anhydride or sodium acetate;

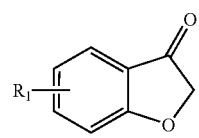

iii) preparing compound of formula (I) according to Fisher-indole reaction by coupling the substituted phenyl hydrazine in the presence of ethanol or p-TsOH solvent.

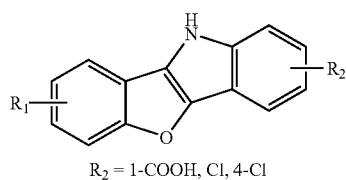

$R_2$ = 1-COOH, Cl, 4-Cl wherein,
$R_1$ is 4-CF$_3$, 4-H, $R_2$ is 1-COOH, 1-Cl, 3-Cl, 4-Cl.

BRIEF DESCRIPTION OF THE DRAWINGS

FIG. 6A illustrates concentration-dependence activity of rSlo channel. FIG. 6B illustrates concentration-dependence activity of rSlo channel combined with human β1. FIG. 6C illustrates concentration-dependence activity of rSlo channel combined with rat β4 subunit.

BEST MODE FOR CARRYING OUT THE INVENTION

Figure 1:
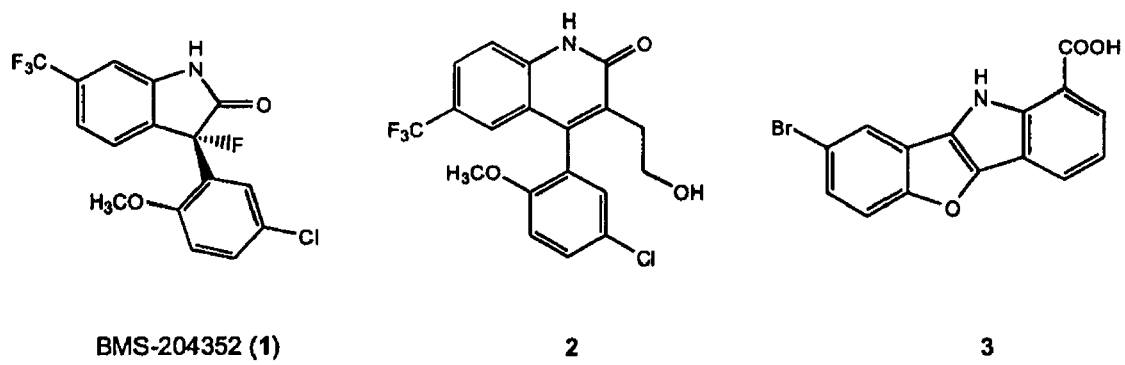
FIG. 1 illustrates chemical structures of BK$_{Ca}$ channel openers of present invention.

The present invention can be described in detail as follows.

An idea of positioning of appropriate functional groups was obtained from the comparison of low energy conformers of a potent BK$_{Ca}$ channel opener 1 (BMS-204352) and benzofuroindole skeleton as shown in the superimposed structure (FIG. 2) with semi-empirical calculations by using MOPAC 2002 protocol.

Trifluoromethyl and chloro groups were accordingly selected for the substitution at 7 and 4 positions of benzofuroindole template, respectively. Also, synthesis of other benzofuroindole series with different functional groups were included as briefly depicted in Scheme 1 to determine the structure activity relationships.

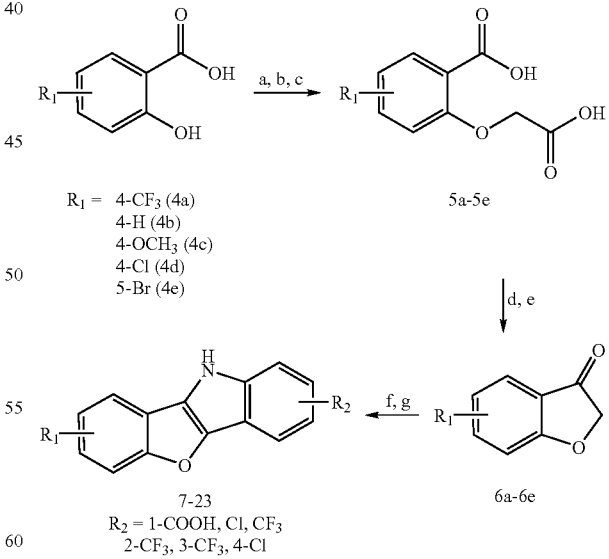

Scheme 1

$R_1$ = 4-CF$_3$ (4a)
4-H (4b)
4-OCH$_3$ (4c)
4-Cl (4d)
5-Br (4e)

$R_2$ = 1-COOH, Cl, CF$_3$
2-CF$_3$, 3-CF$_3$, 4-Cl (a) CH$_3$OH, H$_2$SO$_4$, reflux, 12 hr, yield 95~98%, (b) Ethyl bromoacetate, K$_2$CO$_3$, acetone, reflux, 24 hr, yield 70~76%, (c) 10% aqueous NaOH in CH$_3$OH, 25° C., 5 hr, yield 80~87%, (d) Ac₂O, AcOH, CH₃COONa, reflux, 8 hr, yield 70~75%, (e) 1N-HCl, H₂O, CH₃OH, reflux, 7 hr, yield 55~65%, (f) substituted phenylhydrazines, C₂H₅OH, H₂O, 25° C., 5 hr, yield 2 2~35%, (g) p-TsOH, C₂H₅OH, 80° C., 18 h or microwave, 1~2 min, yield 6 4~77%.

Salicylic esters obtained from Fisher esterification of commercially available substituted salicylic acids were alkylated with ethylbromoacetate and subsequent double-branch hydrolysis gave 5a~e. Cyclizations under the reflux condition with acetic anhydride, sodium acetate and acetic acid followed by acidification to remove acetate group from the enol-acetate intermediate to benzofuranones, 6a~e. The benzofuranones were couple with various substituted phenylhydrazines to afford corresponding hydrazones, which were subjected to Fisher-indole reaction to convert into benzofuroindole derivatives, 7~23 in reflux condition or microwave reaction with acid catalysts. Table 1 shows the various benzofuroindole derivatives obtained according to above method.

TABLE 1

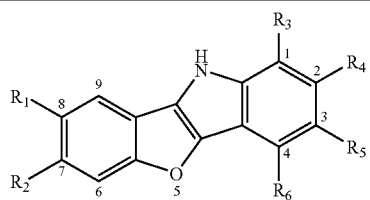

| Compound No. | $R_1$ | $R_2$ | $R_3$ | $R_4$ | $R_5$ | $R_6$ |
|---|---|---|---|---|---|---|
| 7 | Br | H | COOH | H | H | H |
| 8 | H | CF₃ | COOH | H | H | H |
| 9 | H | CF₃ | H | H | CF₃ | H |
| 10 | H | CF₃ | H | H | H | CF₃ |
| 11 | H | CF₃ | Cl | H | H | H |
| 12 | H | CF₃ | CF₃ | H | H | H |
| 13 | H | H | COOH | H | H | H |
| 14 | H | CF₃ | OCH₃ | H | H | H |
| 15 | H | CF₃ | COOCH₃ | H | H | H |
| 16 | H | OCH₃ | COOH | H | H | H |
| 17 | H | Cl | COOH | H | H | H |
| 18 | H | CF₃ | Cl | Cl | H | H |
| 19 | H | CF₃ | H | Cl | H | Cl |
| 20 | H | CF₃ | H | H | H | F |
| 21 | H | CF₃ | H | F | H | H |
| 22 | H | CF₃ | COOH | H | H | Cl |
| 23 | H | CF₃ | COOH | H | Cl | H |

The biological activity of compounds 7~23 to open $BK_{Ca}$ channels and increase the $BK_{Ca}$ channel currents was determined by using excised outside-out voltage clamp recording from *Xenopus laevis* oocytes expressing cloned α subunit of rat $BK_{Ca}$ channels, rSlo.

The advantageous effect of the present invention is to provide a potassium channel opener having benzofuroindole skeleton. The inventors report an optimization of the pharmacophores in benzofuroindole skeleton for $BK_{Ca}$ channel opening activity from the synthesis of a series of substituted benzofuroindole derivatives and the electrophysiological property with $Ca^{2+}$ independent manner.

The present invention can be explained more concretely by following examples. However, the scope of present invention shall not be limited by following examples.

EXAMPLES

Preparation Example 1

7-Trifluoromethyl-10H-benzo[4,5]furo[3,2-b]indole-1-carboxylic acid (compound 8)

2-Carboxymethoxy-4-trifluoromethyl-benzoic acid (product 5a): An agitated mixture of methanol (80 ml), concentrated sulfuric acid (6.7 ml), 2-hydroxy-4-trifluoromethyl-benzoic acid (31.2 g) was heated at reflux for 12 hrs. After cooling to room temperature, the mixture was worked-up with sodium bicarbonate and ethyl acetate. 2-Hydroxy-4-trifluoromethyl-benzoic acid methyl ester from ethyl acetate layer was purified by chromatography (Hexane:EA=10:1).

Anhydrous potassium carbonate (29 g) was added to an agitated solution of hydroxy-4-trifluoromethyl-benzoic acid methyl ester (32.5 g) in dry acetone (100 ml). Ethyl bromo acetate (25 ml) was then added dropwise and the mixture was heated at reflux (14 hrs). After cooling to room temperature, the solution was worked up with water and ethyl acetate. 2-Ethoxycarbonylmethoxy-4-trifluoromethyl-benzoic acid methyl ester from ethyl acetate layer was then purified by chromatography (Hexane:EA=15:1).

A mixture of 2-Ethoxycarbonylmethoxy-4-trifluoromethyl-benzoic acid methyl ester (34 g), 10% NaOH (132.5 g) and methanol (45 ml) were mixed in one necked round flask. Resulting mixture was mixed at room temperature for 5 hrs. Acidified to pH 2 by 1 N HCl. Evaporated in vacuo. Filtrated and washed with water to obtain the product 5a.

6-Trifluoromethyl-benzofuran-3-one (product 6a): A well agitated mixture of acetic anhydride (95 ml), acetic acid (14 ml) anhydrous sodium acetate (10.7 g) and 5a was heated to reflux for 7 hrs. The mixture was then cooled to room temperature and worked-up with water and ethyl acetate. The remaining acetic anhydride was co-evaporated with ethyl acetate. Then, crude product was purified by chromatography to give acetic acid 6-trifluoromethyl-benzofuran-3-yl ester (Hexane:EA=10:1).

A mixture of acetic acid 6-trifluoromethyl-benzofuran-3-yl ester (15 g), methanol (100 ml), water (53.8 ml) and 1 N HCl (18.8 ml) was heated at reflux for 6 hrs. Mixture was cooled to room temperature. Crude product was evaporated in vacuo and purified by chromatography to give product 6a (Hexane:EA=18:1).

7-Trifluoromethyl-10H-benzo[4,5]furo[3,2-b]indole-1-carboxylic acid (compound 8): 150 mg 6a was dissolved in ethanol (5.2 ml) and 2-hydrazino benzoic acid was dissolved in water (10.3 ml). These two homogenous mixtures were mixed together and stirred at room temperature for 4 hrs. Precipitation is filtered and first washed with water and then ethanol. The filtrate was put in vacuum oven for 4 hrs for complete evaporation. The mixture of 2-[N'-(6-trifluoromethyl-benzofuran-3-yl-idene)-hydrazino]-benzoic acid (120 mg), p-TsOH (1~2 Eqv) and ethanol (5 ml) were refluxed for 30 hrs. Cooled to room temperature and evaporated in vacuo. Resulting mixture was purified by chromatography to afford compound 8 (CHCl₃:MeOH=30:1).

Yield: 64.4% (3.94 g). ¹H NMR (300 MHz, DMSO) δ (ppm) 11.80 (s, 1H), 8.29 (d, J=8.4 Hz, 1H), 8.15 (s, 1H), 8.11 (d, J=7.5 Hz, 1H), 7.95 (d, J=7.5 Hz, 1H), 7.71 (d, J=8.4 Hz, 1H), 7.30 (t, J=8.4 Hz, 1H), MS (ESI) m/z: 319.23 ([M+H]⁺)

Preparation Example 2

Following compounds were prepared as the same manner disclosed in Preparation Example 1. The chemical name of obtained compound, yield, NMR peak data and molecular weight measured by MS (mass spectroscopy) are described as follows.

8-Bromo-10H-benzo[4,5]furo[3,2-b]indole-1-carboxylic acid (compound 7)

Yield: 64.4% (3.94 g). $^1$H NMR (300 MHz, DMSO) δ (ppm) 11.8 (s, 1H), 8.28 (s, 1H), 8.09 (d, J=7.8 Hz, 1H), 7.93 (d, J=7.8 Hz, 1H), 7.72 (d, J=9 Hz, 1H), 7.53 (d, J=9 Hz, 1H), 7.31 (t, J=7.8 Hz, 1H), MS (ESI) m/z: 330.13 ([M+H]$^+$)

3,7-Bis-trifluoromethyl-10H-benzo[4,5]furo[3,2-b]indole (compound 9)

Yield: 64.4% (3.94 g). $^1$H NMR (300 MHz, CDCl$_3$) δ (ppm) 8.44 (s, 1H), 7.97 (d, J=7.8 Hz, 1H), 7.92 (s, 1H), 7.84 (d, J=8.1 Hz, 1H), 7.80 (s, 1H), 7.63 (d, J=8.1 Hz, 1H), 7.53 (d, J=7.8 Hz, 1H), MS (ESI) m/z: 343.22 ([M+H]$^+$)

4,7-Bis-trifluoromethyl-10H-benzo[4,5]furo[3,2-b]indole (compound 10)

Yield: 64.4% (3.94 g). $^1$H NMR (300 MHz, CDCl$_3$) δ (ppm) 8.47 (s, 1H), 8.00 (s, 1H), 7.8 (d, J=8.1 Hz, 1H), 7.72 (d, J=8.1 Hz, 1H), 7.64 (d, J=7.5 Hz, 1H), 7.57 (d, J=7.5 Hz, 1H), 7.44 (t, J=7.5, 1H), MS (ESI) m/z: 343.22 ([M+H]$^+$)

1-Chloro-7-trifluoromethyl-10H-benzo[4,5]furo[3,2-b]indole (compound 11)

Yield: 64.4% (3.94 g). $^1$H NMR (300 MHz, CDCl$_3$) δ (ppm) 8.46 (s, 1H), 7.90 (s, 1H), 7.81 (d, J=8.1 Hz, 1H), 7.80 (d, J=8.1 Hz, 1H), 7.62 (d, J=7.8 Hz, 1H), 7.35 (d, J=7.8 Hz, 1H), 7.20 (t, J=7.8 Hz, 1H), MS (ESI) m/z: 309.67 ([M+H]$^+$)

1,7-Bis-trifluoromethyl-10H-benzo[4,5]furo[3,2-b]indole (compound 12)

Yield: 64.4% (3.94 g). $^1$H NMR (300 MHz, CDCl$_3$) δ (ppm) 8.63 (s, 1H), 8.09 (d, J=8.1 Hz, 1H), 7.93 (s, 1H), 7.88 (d, J=8.1 Hz, 1H), 7.66 (d, J=7.5 Hz, 1H), 7.63 (d, J=7.5 Hz, 1H), 7.37 (t, J=7.5 Hz, 1H), MS (ESI) m/z: 343.22 ([M+H]$^+$)

10H-Benzo[4,5]furo[3,2-b]indole-1-carboxylic acid (compound 13)

Yield: 64.4% (3.94 g). $^1$H NMR (300 MHz, DMSO) δ (ppm) 11.65 (s, 1H), 8.19 (t, J=4.5 Hz, 1H), 8.04 (d, J=7.5 Hz, 1H), 7.9 (d, J=7.5 Hz, 1H), 7.71 (t, J=4.5 Hz, 1H), 7.38 (d, J=7.5 Hz, 1H), 7.36 (d, J=4.5 Hz, 1H), 7.26 (t, J=7.5 Hz, 1H), MS (ESI) m/z: 251.24 ([M+H]$^+$)

1-Methoxy-7-trifluoromethyl-10H-benzo[4,5]furo[3,2-b]indole (compound 14)

Yield: 64.4% (3.94 g). $^1$H NMR (300 MHz, CDCl$_3$) δ (ppm) 8.35 (s, 1H), 7.87 (s, 1H), 7.77 (d, J=8.1 Hz, 1H), 7.58 (d, J=8.1 Hz, 1H), 7.48 (d, J=7.8 Hz, 1H), 7.17 (t, J=7.8 Hz, 1H), 6.8 (d, J=7.8 Hz, 1H), 4.03 (s, 3H), MS (ESI) m/z: 305.25 ([M+H]$^+$)

7-Trifluoromethyl-10H-benzo[4,5]furo[3,2-b]indole-1-carboxylic acid methyl ester (compound 15)

Yield: 64.4% (3.94 g). $^1$H NMR (300 MHz, CDCl$_3$) δ (ppm) 10.11 (s, 1H), 8.1 (d, J=7.5 Hz, 1H), 8.04 (d, J=7.5 Hz, 1H), 7.90 (s, 1H), 7.85 (d, J=8.1 Hz, 1H), 7.62 (d, J=8.1 Hz, 1H), 7.30 (t, J=8.1 Hz, 1H), 4.05 (s, 3H), MS (ESI) m/z: 333.26 ([M+H]$^+$)

7-Methoxy-10H-benzo[4,5]furo[3,2-b]indole-1-carboxylic acid (compound 16)

Yield: 64.4% (3.94 g). $^1$H NMR (300 MHz, DMSO) δ (ppm) 11.54 (s, 1H), 7.99 (d, J=8.4 Hz, 1H), 7.96 (d, J=8.4 Hz, 1H), 7.83 (d, J=7.5 Hz, 1H), 7.33 (s, 1H), 7.22 (t, J=7.5 Hz, 1H), 7.00 (d, J=7.5 Hz, 1H), MS (ESI) m/z: 281.26 ([M+H]$^+$)

7-Chloro-10H-benzo[4,5]furo[3,2-b]indole-1-carboxylic acid (compound 17)

Yield: 64.4% (3.94 g). $^1$H NMR (300 MHz, DMSO) δ (ppm) 11.82 (s, 1H), 8.09 (d, J=7.2 Hz, 1H), 8.04 (d, J=7.2 Hz, 1H), 7.91 (d, J=7.8 Hz, 1H), 7.89 (s, 1H), 7.44 (d, J=7.8 Hz, 1H), 7.29 (t, J=7.8 Hz, 1H), MS (ESI) m/z: 285.68 ([M+H]$^+$)

1,2-Dichloro-7-trifluoromethyl-10H-benzo[4,5]furo[3,2-b]indole (compound 18)

Yield: 64.4% (3.94 g). $^1$H NMR (300 MHz, CDCl$_3$) δ (ppm) 8.46 (s, 1H), 7.89 (s, 1H), 7.82 (d, J=8.4 Hz, 1H), 7.71 (d, J=8.4 Hz, 1H), 7.63 (d, J=8.4 Hz, 1H), 7.35 (d, J=8.4 Hz, 1H), MS (ESI) m/z: 344.11 ([M+H]$^+$)

2,4-Dichloro-7-trifluoromethyl-10H-benzo[4,5]furo[3,2-b]indole (compound 19)

Yield: 64.4% (3.94 g). $^1$H NMR (300 MHz, CDCl$_3$) δ (ppm) 8.31 (s, 1H), 7.95 (s, 1H), 7.79 (d, J=8.1 Hz, 1H), 7.62 (d, J=8.1 Hz, 1H), 7.41 (s, 1H), 7.26 (s, 1H), MS (ESI) m/z: 344.11 ([M+H]$^+$)

4-Fluoro-7-trifluoromethyl-10H-benzo[4,5]furo[3,2-b]indole (compound 20)

Yield: 64.4% (3.94 g). $^1$H NMR (300 MHz, CDCl$_3$) δ (ppm) 8.15 (s, 1H), 7.87 (s, 1H), 7.79 (d, J=9.00 Hz, 1H), 7.75 (d, J=8.7 Hz, 1H), 7.59 (d, J=8.7 Hz, 1H), 7.21 (d, J=9.00 Hz, 1H), 7.03 (t, J=9.00 Hz, 1H), MS (ESI) m/z: 293.22 ([M+H]$^+$)

2-Fluoro-7-trifluoromethyl-10H-benzo[4,5]furo[3,2-b]indole (compound 21)

Yield: 64.4% (3.94 g). $^1$H NMR (300 MHz, CDCl$_3$) δ (ppm) 8.25 (s, 1H), 7.92 (s, 1H), 7.78 (d, J=8.1 Hz, 1H), 7.61 (d, J=8.1 Hz, 1H), 7.30 (d, J=6.6 Hz, 1H), 7.20 (s, 1H), 6.95 (d, J=6.6 Hz, 1H), MS (ESI) m/z 293.22 ([M+H]$^+$)

4-Chloro-7-trifluoromethyl-10H-benzo[4,5]furo[3,2-b]indole-1-carboxylic acid (compound 22)

Yield: 64.4% (3.94 g). $^1$H NMR (300 MHz, DMSO) δ (ppm) 12.08 (s, 1H), 8.32 (d, J=8.4 Hz, 1H), 8.4 (s, 1H), 7.92 (d, J=8.4 Hz, 1H), 7.77 (d, J=8.1 Hz, 1H), 7.37 (d, J=8.1 Hz, 1H), MS (ESI) m/z: 353.68 ([M+H]$^+$)

3-Chloro-7-trifluoromethyl-10H-benzo[4,5]furo[3,2-b]indole-1-carboxylic acid (compound 23)

Yield: 64.4% (3.94 g). $^1$H NMR (300 MHz, DMSO) δ (ppm) 11.97 (s, 1H), 8.30 (d, J=8.1 Hz, 1H), 8.23 (s, 1H), 8.18 (s, 1H), 7.85 (s, 1H), 7.76 (d, J=8.1 Hz, 1H), MS (ESI) m/z: 353.68 ([M+H]$^+$)

Example 1

Figure 3:
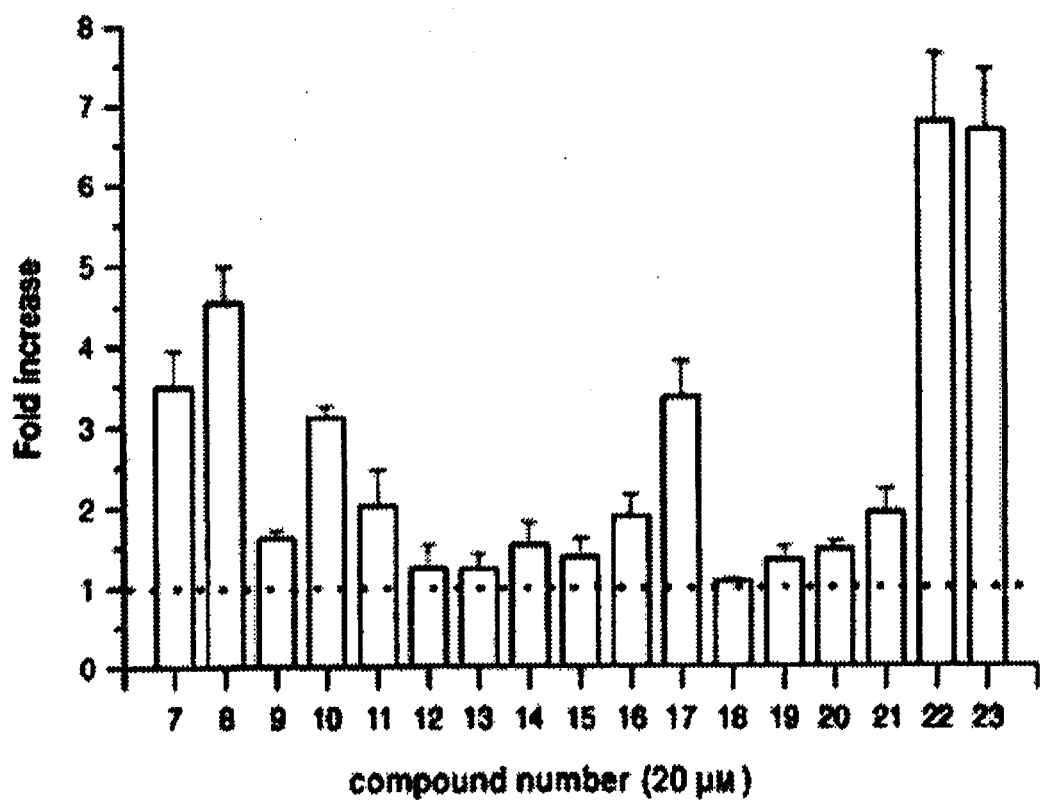
FIG. 3 illustrates relative fold-increase of BK$_{Ca}$ channel activity by extracellularly applied benzofuroindole analogues of present invention. Bar graphs represent fold increases in BK$_{Ca}$ channel currents evoked by extracellular treatment of various compounds at 20 μM.

Measuring the Current of Potassium Channel of Compound of the Present Invention The relative fold increases of $BK_{Ca}$ channel currents by synthesized compounds were shown in FIG. 3. By comparing the channel opening activity of compounds 7, 8, 13, 16 and 17, substitution at 7 or 8 position with bromo, trifluoromethyl or chloro groups showed more than 3 fold increase of the channel currents, while no substitution or electron donating group such as methoxy group at 7 position provided much less potency.

Thus, it appears that electron withdrawing substituents on the side of benzofuranone is essential for the activity. Among these functional groups, trigfluoromethyl, the overlapping functional group with BMS-204352 shown in FIG. 2, conferred the highest opening activity. For the substituents at the position 1, the carboxylic acid was turned out to be significantly important for the activity when 8 was compared with 11 (chloro), 12 (trifluoromethyl), 14 (methoxy) and 15 (methyl ester).

Figure 2:
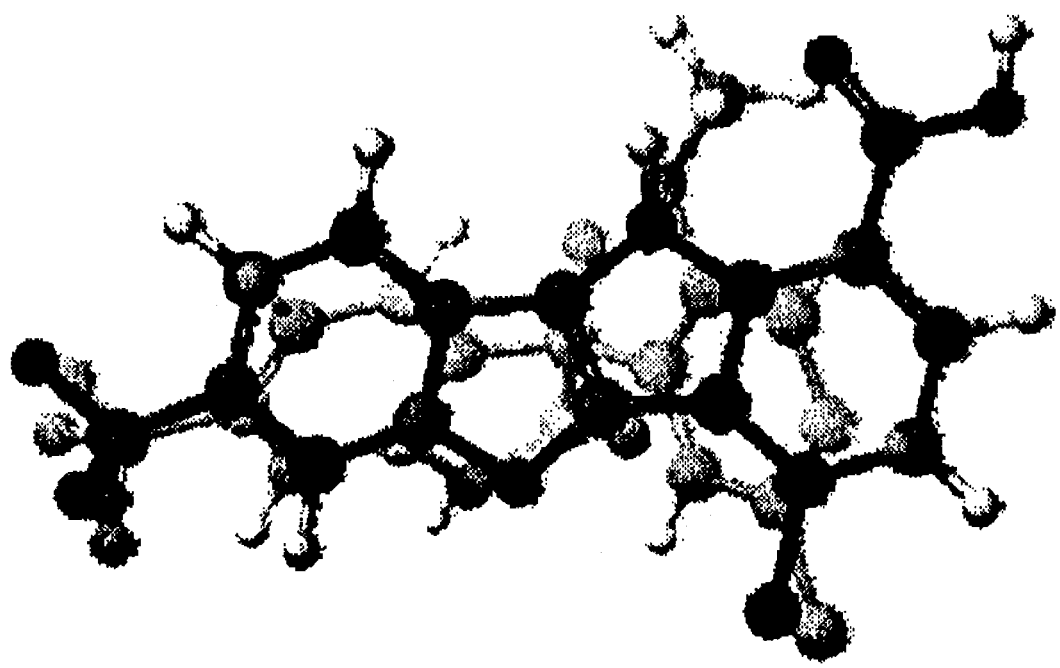
FIG. 2 illustrates a superimposed structure of benzofuroindole compound of present invention and BMS-2043552.

In the case of trifluoromethyl substituents at various positions of the indole ring side such as 9, 10 and 12, the most active position was 4 (compound 10), indicating the overlapped structure with BMS-204352 in FIG. 2 may provide a clue to improve the activity. Other derivatives of chloro and fluoro substituents, 18, 19, 20 and 21 displayed the activity near to the basal level.

Compound 22, containing carboxylic acid group at position 1 and chloride group at the overlapped position 4 with BMS-204352 showed more than 6 fold increase of channel opening activity, which should be resulted in the synergistic effects of appropriate double substitutions at position 1 and 4. Compound 23 having chloride group at position 3 was also displayed close but not better channel opening activity than compound 22.

Considering that the reported fold increases of BMS-204352 and compound 2 are around 1.5 and 3.7, respectively in the similar assay system with the same concentration (20 μM) of compounds, the potency of compound 22 and 23 is remarkable.

Example 2

Measuring the Activity of Compound of the Present Invention on Cloned Vector $BK_{Ca}$ (rSlo) Channel To investigate the potentiating effect of compound 22 on rSlo channels at various intracellular $Ca^{2+}$ concentrations, rSlo channels were activated in different concentrations of intracellular $Ca^{2+}$.

Excised outside-out patch configurations were obtained by making a gigaohm seal, rupturing the membrane pulling the pipette from *oocytes*. Both of the bath and pipette contained symmetrical 124 mM K$^+$ ions. Voltage pulses were applied to activate rSlo channel currents from −120 mV to 140 mV in 10 mV increments and intracellular $Ca^{2+}$ concentrations were used to activate rSlo channel from 0 ($Ca^{2+}$-free solution was to chelate with 5 mM EGTA) to 2 μM in intracellular side.

Figure 4:
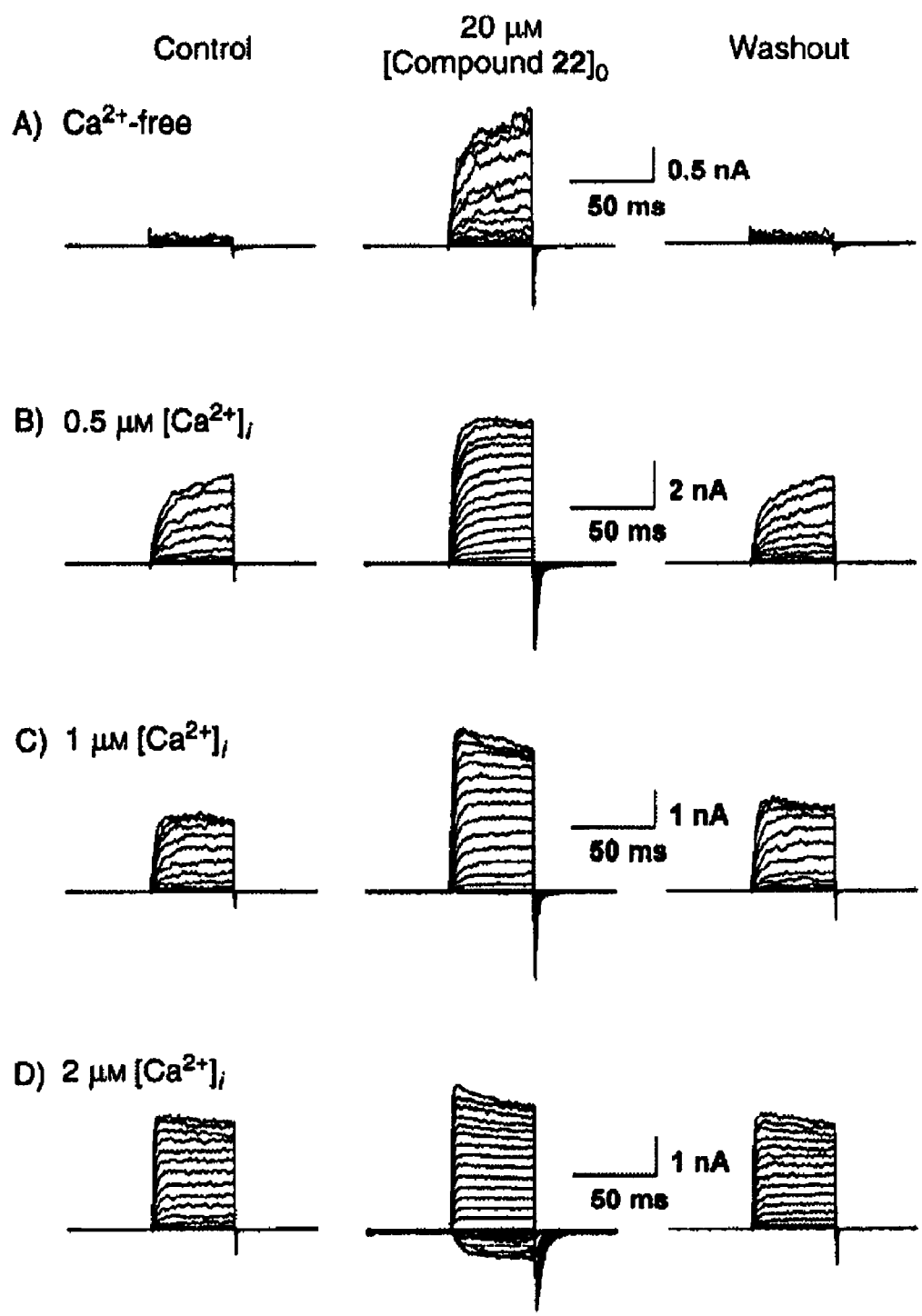
FIG. 4 illustrates potency of extracellularly applied compound 22 on rSlo channels in various intracellular Ca$^{2+}$ concentrations. Representative raw-traces were shown at different intracellular Ca$^{2+}$ concentrations. Intracellular Ca$^{2+}$ concentration was increased from Ca$^{2+}$-free (A), 0.5 μM (B), 1 μM (C) and 2 μM (D). The concentration of compound 22 was 20 μM on the extracellular side.

The representative raw-traces of rSlo channel activated by membrane voltages and intracellular $Ca^{2+}$ (FIG. 4). rSlo channel currents were recorded before and after the addition of 20 μM of compound 22. Compound 22 showed markedly significant effects on rSlo channel current at concentration of 20 μm in various concentrations of intracellular $Ca^{2+}$ These enhanced effects of rSlo current by compound 22 could be removed by washout. FIG. 4 shows markedly induced rSlo channel currents by extracellularly applied compound 22 and it is recovered after the washout in tested entire concentrations of intracellular $Ca^{2+}$. These results suggest that intracellular $Ca^{2+}$ concentrations do not affect the potentiating effect of compound 22 on rSlo channels.

From these results, we can assume that the neuronal $BK_{Ca}$ channels can be activated by compound 22 even at the resting membrane potentials of about −60~−80 mV in the presence of marginal free $Ca^{2+}$ concentration of under 100 nM.

Example 3

Measuring the Activity of Compound of the Present Invention on *Xenopus Oocytes*

We performed experiments to determine the concentration dependence for the effect of compound 22 on macroscopic rSlo channel activity expressed in *Xenopus oocytes*.

Figure 5:
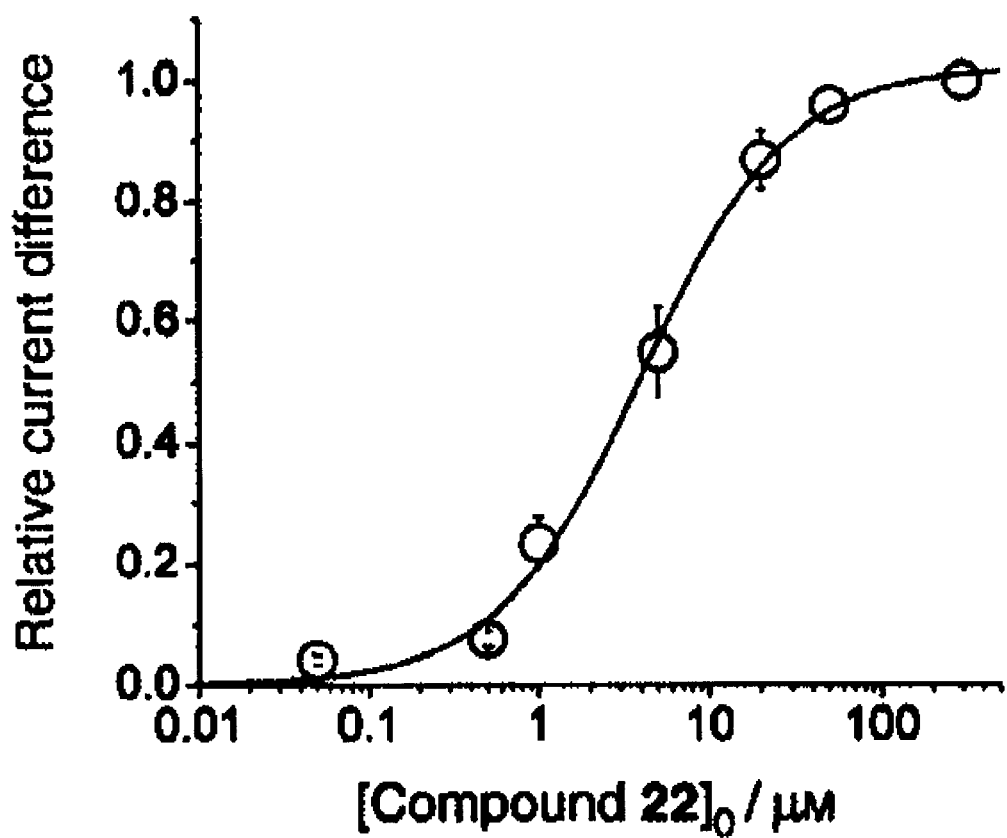
FIG. 5 illustrates concentration-dependence of compound 22 on BK$_{Ca}$ channel. Data points were fitted with Hill equation. The K$_d$, the apparent dissociation constant of compound 22, obtained from the best fitting was 4.01±0.75 μM, and the n values, the Hill coefficient constant, was 1.02±0.07 (N=5, p<0.01).

Currents were recorded from excised outside-out patches before and after the addition of seven different concentrations of compound 22, from 0 to 300 μM. Channel activity of rSlo was elicited after patch excision with 2 μM intracellular $Ca^{2+}$ and increased rapidly with the addition of compound 22. Membrane potential was held at −120 mV and stepped to 50 mV for 50 ms. Relative current differences were determined from the currents of control activated with 2 μM of intracellular $Ca^{2+}$ and voltage at 50 mV, normalized with control currents and the obtained data points were fitter with a Hill equation (FIG. 5).

Addition of compound 22 in the range of 50 nM to 300 μM enhanced rSlo current in a concentration dependent manner. The normalized relative current-fold increase were well fitted with the Hill equation. The $K_d$, the apparent dissociation constant of compound 22, obtained from the best fitting was 4.01±0.75 μM and the n value, the Hill coefficient constant, was 1.20±0.07 (N=5, p<0.01). Theses results suggest that compound 22 should bind rSlo channel in one-to-one ratio. Further detailed of biological activity and mechanism of the benzofuroindole derivatives on the channel will be reported elsewhere.

In summary, benzofuroindole skeleton was compared with a known $BK_{Ca}$ channel opener, BMS-204352, to optimizer pharmacophore groups to be incorporated. Being evaluated on the cloned $BK_{Ca}$ channels by utilizing outside-out patches of rSlo channel expressed in *Xenopus laevis oocytes*, compound 22 was identified as the potent and effective $BK_{Ca}$ channel openers with intracellular calcium independent manner. The $BK_{Ca}$ channel opener might be further applied to the therapeutic interventions in stroke, asthma, hypertension, convulsion and traumatic brain injury.

Example 4

Figure 6:
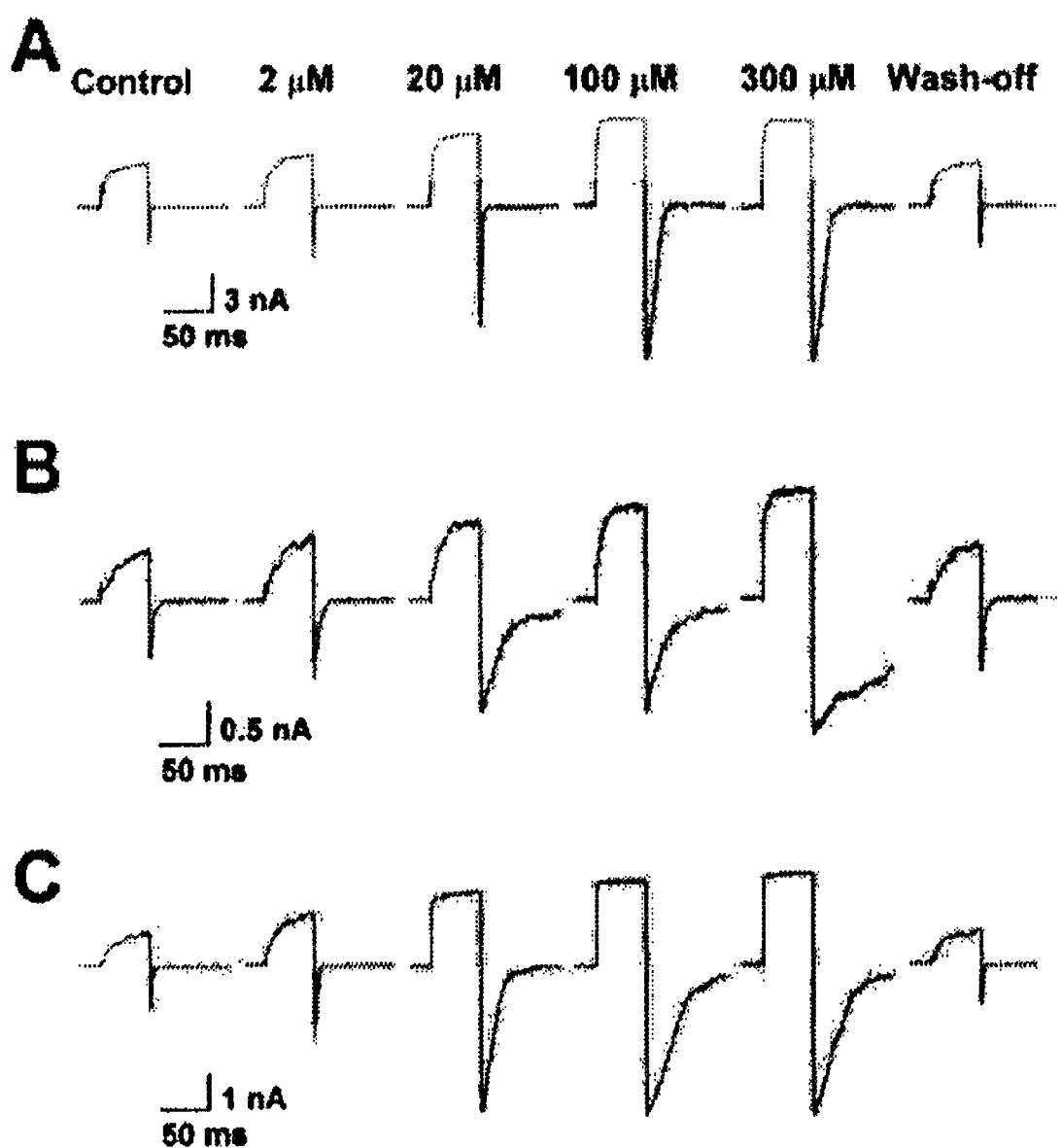
FIG. 6 illustrates concentration-dependence activity of compound 8 on BK$_{Ca}$ channel.

Measuring the Activity of Concentration-Dependence Channel Opening of Compound of the Present Invention We then measured the concentration-dependence of compound 8 of the present invention. As increasing concentrations of compound 8 were applied to the extracellular side of membrane patched, the activation rate as well as the level of steady-state current was increased in a concentration-dependent manner (FIG. 6A). Although we were not able to obtain a concentration of compound 8 higher than 300 μM because of its solubility in water, we noticed that compound 8-induced current increases reached plateau levels at around 100 μM. The concentration of $EC_{50}$ of compound 8 for rSlo channel was determined as 8.9±1.5 μM. We also measured the effects of compound 8 using inside-out patch configuration to determine whether this compound also affects channel activity from the intracellular side. The intracellular $Ca^{2+}$ concentration was fixed at 2 μM to activate rSlo channels, and different concentrations of compound 8 were added to the intracellular side of the membrane. Although intracellular compound 8 also increased rSlo currents with a similar apparent affinity, its-fold increase was much smaller than that obtained from extracellular side.

The functional characteristic of $BK_{Ca}$ channels are altered by auxiliary β subunits, and the efficacy of some activators and inhibitors is greatly influenced by coassembly of βsubunits. Thus, we asked whether the potentiating effects of compound 8 are affected by coexpression of β subunits. We expressed rSlo together with either human β1 or rat β4 subunit in *Xenopus laevis oocytes* and measured the channel currents in the presence of difference concentrations of extracellular compound 8. The activities of both rSlo/human β1 (FIG. 6B) and rSlo/rat β4 (FIG. 6C) were increased by micromolar concentration of the compound in a concentration-dependence manner. However, these results indicate that compound 8 can potentiate $BK_{Ca}$ channel without the coassembly of β subunits and argue that the receptor site of compound 8 locates within the main subunit of $BK_{Ca}$ channel, the Slo protein.

What is claimed is:

1. A potassium channel opener having benzofuroindole skeleton representing the following formula (I)

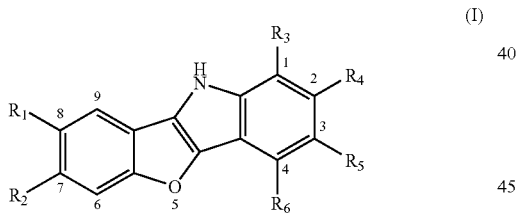

wherein,
$R_1$ is hydrogen, $R_2$ is $CF_3$, $R_3$ is COOH, $R_4$ is hydrogen, $R_5$ is hydrogen or chloride and $R_6$ is hydrogen or chloride.

2. The potassium channel opener having benzofuroindole skeleton according to claim 1, wherein $R_1$ is hydrogen, $R_2$ is $CF_3$, $R_3$ is COOH, $R_4$ is hydrogen, $R_5$ is hydrogen and $R_6$ is hydrogen.

3. The potassium channel opener having benzofuroindole skeleton according to claim 1, wherein $R_1$ is hydrogen, $R_2$ is $CF_3$, $R_3$ is COOH, $R_4$ is hydrogen, $R_5$ is hydrogen and $R_6$ is chloride.

4. The potassium channel opener having benzofuroindole skeleton according to claim 1, wherein $R_1$ is hydrogen, $R_2$ is $CF_3$, $R_3$ is COOH, $R_4$ is hydrogen, $R_5$ is chloride and $R_6$ is hydrogen.

5. A process for preparing a potassium channel opener having benzofuroindole skeleton representing the following formula (I), which comprises the steps of:
i) preparing compound of formula (III) by reacting and condensing salicylic acid derivatives represented by formula (II) as starting material

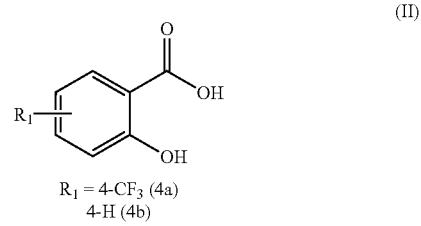

$R_1 = 4\text{-}CF_3$ (4a)
4-H (4b)

with ethylbromoacetate in the present of sulfuric acid added methanol solvent leaving the hydrogen bromide subsequently and leaving the ethyl group by NaOH aqueous solution;

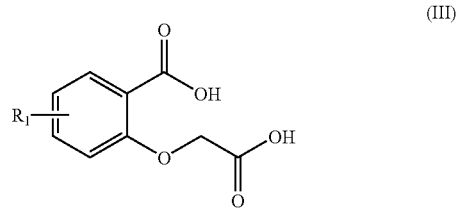

ii) preparing compound of formula (IV) by cyclization reaction through the reflux of compound of formula (III) in the presence of acetic anhydride or sodium acetate;

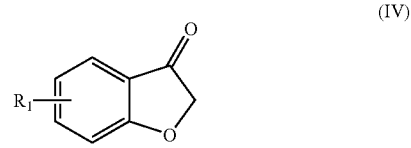

iii) preparing compound of formula (I) according to Fisher-indole reaction by coupling the substituted phenyl hydrazine in the presence of ethanol or p-TsOH solvent;

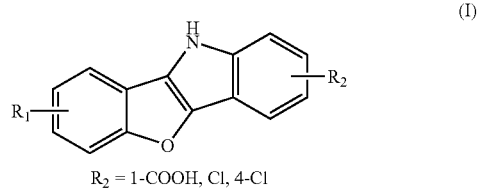

$R_2 = 1\text{-}COOH, Cl, 4\text{-}Cl$ wherein,
$R_1$ is 4-$CF_3$, 4-H, $R_2$ is 1-COOH, 1-Cl, 3-Cl, 4-Cl.

* * * * *